(12) United States Patent
Ting et al.

(10) Patent No.: US 8,871,978 B2
(45) Date of Patent: Oct. 28, 2014

(54) PREPARATION OF HOP ACIDS AND THEIR DERIVATIVES

(75) Inventors: Patrick L. Ting, Brookfield, WI (US);
Jason Pratt, Milwaukee, WI (US);
David S. Ryder, Mequon, WI (US)

(73) Assignee: MillerCoors LLC, Wilmington, DE (US)

( * ) Notice: Subject to any disclaimer, the term of this patent is extended or adjusted under 35 U.S.C. 154(b) by 543 days.

(21) Appl. No.: 13/112,770

(22) Filed: May 20, 2011

(65) Prior Publication Data

US 2011/0288335 A1     Nov. 24, 2011

Related U.S. Application Data

(60) Provisional application No. 61/347,201, filed on May 21, 2010.

(51) Int. Cl.
| | | |
|---|---|---|
| *C07C 45/85* | (2006.01) | |
| *C12C 3/12* | (2006.01) | |
| *A61K 31/122* | (2006.01) | |

(52) U.S. Cl.
CPC . *C12C 3/12* (2013.01); *C07C 45/85* (2013.01); *A61K 31/122* (2013.01)
USPC ........................................................ 564/303

(58) Field of Classification Search
CPC ......... C07C 45/85; A61K 31/122; C12C 3/12
USPC ........................................................ 564/303
See application file for complete search history.

(56) References Cited

U.S. PATENT DOCUMENTS

| | | |
|---|---|---|
| 3,923,897 A | 12/1975 | Worden |
| 4,644,084 A | 2/1987 | Cowles et al. |
| 5,523,489 A | 6/1996 | Ting et al. |
| 5,767,319 A | 6/1998 | Ting et al. |
| 6,020,019 A | 2/2000 | Ting et al. |
| 6,303,824 B1 | 10/2001 | Ting et al. |
| 7,270,835 B2 | 9/2007 | Tripp et al. |
| 7,388,098 B2 | 6/2008 | Venit et al. |

FOREIGN PATENT DOCUMENTS

| | | |
|---|---|---|
| GB | 1158697 | 7/1969 |
| GB | 1266716 | 3/1972 |
| WO | 96/36584 | 11/1996 |
| WO | 2010/008299 | 1/2010 |

OTHER PUBLICATIONS

Ting, Patrick L. and Henry Goldstein. "Preparation and Purification of Hop Acids and their Derivatives." American Society of Brewing Chemists 54(2): pp. 103-109, 1996.
Kinbara, Kazushi; Kobayashi, Yuko; Saigo, Kazuhiko. "Chiral discrimination of 2-arylalkanoic acids by (1S,2R)-1-arninoindan-2-ol through the formation of a consistent columnar supramolecular hydrogen-bond network." J. Chem. Soc. Perkins Trans. 2: pp. 111-119, 2000.
De Keukeleire, Denis. "Fundamentals of Beer and Hop Chemistry." Quimica Nova 23(1): pp. 108-112, 2000.
International Application No. PCT/US2011/037398. International Search Report and Written Opinion dated Aug. 4, 2011.

*Primary Examiner* — Yong Chu
(74) *Attorney, Agent, or Firm* — Quarles & Brady LLP

(57) ABSTRACT

A method for preparing a hop acid mixture having an enantiomeric excess of a (+)-tetrahydro-α-acid is disclosed. In the method, a racemate of a tetrahydro-α-acid is contacted with an amine to form a precipitate having an enantiomeric excess of the (+)-tetrahydro-α-acid. A method for preparing a hop acid is also disclosed. In the method, a racemate of a tetrahydro-α-acid is contacted with an amine to form a precipitate comprising a (+)-tetrahydro-α-acid, and the (+)-tetrahydro-α-acid is isomerized to a hop acid selected from the group consisting of (+)-trans-tetrahydro-iso-α-acids, (−)-cis-tetrahydro-iso-α-acids, and mixtures thereof, and reduced to (+)-trans-hexahydroiso-α-acids and (−)-cis-hexahydroiso-α-acids. An additive for flavoring a malt beverage is also disclosed. The additive includes a bittering agent selected from the group consisting of (+)-trans-tetrahydro-iso-α-acids, (−)-cis-tetrahydro-iso-α-acids, (+)-trans-hexahydroiso-α-acids, (−)-cis-hexahydroiso-α-acids, and mixtures thereof.

12 Claims, 5 Drawing Sheets

US 8,871,978 B2

PREPARATION OF HOP ACIDS AND THEIR DERIVATIVES

CROSS-REFERENCES TO RELATED APPLICATIONS

This application claims priority from U.S. Patent Application No. 61/347,201 filed May 21, 2010.

STATEMENT REGARDING FEDERALLY SPONSORED RESEARCH

Not Applicable.

BACKGROUND OF THE INVENTION

1. Field of the Invention

This invention relates to novel hop acid compounds that provide improved flavor, foam, and antimicrobial contributions in malt beverages such as beer and active ingredients for health supplements. In particular, the invention relates to methods for preparing a hop acid mixture having an enantiomeric excess of a (+)-tetrahydro-α-acid, methods for preparing (+)-tetrahydro-α-acids that can be isomerized to (+)-trans-tetrahydro-iso-α-acids and (−)-cis-tetrahydro-iso-α-acids, and reduced to (+)-trans-hexahydroiso-α-acids and (−)-cis-hexahydroiso-α-acids and malt beverage bittering agents including the (+)-trans-tetrahydro-iso-α-acids, (−)-cis-tetrahydro-iso-α-acids, (+)-trans-hexahydroiso-α-acids, (−)-cis-hexahydroiso-α-acids, or mixtures thereof.

2. Description of the Related Art

Chiral recognition of substances, i.e. the ability to distinguish a molecular structure from its mirror image, is one of the most important and widespread principles of biological activity. The first molecular event in odor perception is the interaction of an odorant with a receptor. As olfactory receptors have been identified as proteins, i.e. chiral molecules, this interaction should also be enantioselective, meaning that odor receptors should react differently with the two enantiomeric forms of a chiral odorant, leading to differences in odor strength and/or quality. Discrepant enantiomer effects are well-established, with numerous examples in taste perception. For example, limonene is present in both orange and lemon peels and responsible for their different odor characteristics because orange contains the right-handed (+) molecule while lemon contains the left-handed (−) molecule; (S)-(+)-carvone is a molecule with caraway-like odor while its mirror image molecule (R)-(−)-carvone has a spearmint odor. Linalool is one of main key hop flavor components in beer, which optical isomers have great impact on the character of hoppy flavor. (−)-Linalool is perceived with woody, lavender-like aroma, while its mirror image molecule, (+)-linalool, has sweet and citrus-like aroma.

Tetrahydroiso-α-acids (including three major analogs of tetrahydroisocohumulone, tetrahydrohumulone, and tetrahydroadhumulone) have shown more benefits in brewing than their analogous of iso-α-acids, ρ-iso-α-acids, and hexahydroiso-α-acids. Tetrahydroiso-α-acids impart the most bitter intensity, provide more light stability and flavor stability, enhance more foam, and exhibit stronger antimicrobial activity than the other hop bittering compounds in beer. Tetrahydroiso-α-acids are prepared from either α-acids (including three major analogs of cohumulone, n-humulone, and adhumulone) or β-acids (including three major analogs of colupulone, n-lupulone, and adlupulone) (See, P. Ting & H. Goldstein, J. Am. Soc. Brew. Chem. 54(2):103-109, 1996). From the α-acids (humulones), sequential hydrogenation and isomerization reactions or reversed isomerization and hydrogenation reactions of α-acids are involved as shown in FIG. 1, wherein R=CH$_2$CH(CH$_3$)$_2$ for n-humulone, R=CH(CH$_3$)$_2$ for cohumulone, and R=CH(CH$_3$)CH$_2$CH$_3$ for adhumulone. From the β-acids (lupulones), multiple reactions are involved including a sequential hydrogenolysis/hydrogenation reaction of β-acids, oxidation reaction of the hydrogenated desoxy-α-acids and then an isomerization reaction of tetrahydro-α-acids as shown in FIG. 1, wherein R=CH$_2$CH(CH$_3$)$_2$ for n-lupulone, R=CH(CH$_3$)$_2$ for colupulone, and R=CH(CH$_3$)CH$_2$CH$_3$ for adlupulone.

Both methods produce identical molecules of tetrahydroiso-α-acids, but only different from their stereoisomers. Tetrahydroiso-α-acids prepared from α-acids are optically active compounds, or enantiomers, due to the natural structure of α-acids (asymmetry molecules) (see, D. De Keukeleire and M. Verzele, J. Inst. Brewing, 76:265, 1970). However, tetrahydroiso-α-acids prepared from β-acids (no asymmetry molecules) are a racemic mixture (containing pairs of mirror image molecules or equal opposite enantiomers) with no optical activity (see, Patrick L. Ting and Henry Goldstein, J. Am. Soc. Brew. Chem. 54(2):103-109, 1996).

The molecular perception of stereochemistry of tetrahydroiso-α-acids and hexahydroiso-α-acids prepared from either α-acids or β-acids is very important because of their potential flavor, foam, antimicrobial contributions in beer as well as important ingredients for nutraceuticals and functional food (see U.S. Pat. No. 7,270,835). However, the stereochemistry and physiological properties (chiral recognition) have not been investigated and reported for tetrahydroiso-α-acids prepared from β-acids.

Therefore, there still exists a need for tetrahydroiso-α-acid compounds that improve flavor, foam, and antimicrobial contributions in malt beverages such as beer.

SUMMARY OF THE INVENTION

In one aspect, the invention provides a method for preparing a hop acid mixture having an enantiomeric excess of a (+)-tetrahydro-α-acid. In the method, a racemate of a tetrahydro-α-acid is contacted with an amine to form a precipitate having an enantiomeric excess of the (+)-tetrahydro-α-acid. The precipitate can be treated to prepare a solid having an enantiomeric excess of the (+)-tetrahydro-α-acid of greater than 50%, or more preferably greater than 80%. The amine can be a chiral amine such as (1S,2R)-(−)-cis-1-amino-2-indanol. The racemate of the tetrahydro-α-acid can be prepared by hydrogenating a β-acid to prepare a desoxy-α-acid, and oxidizing and isomerizing the hydrogenated desoxy-α-acid to prepare the racemate of the tetrahydro-α-acid. In one version of the method, the β-acid is colupulone, and the desoxy-α-acid is tetrahydrodesoxycohumulone. The tetrahydro-α-acid can be selected from tetrahydrohumulone, tetrahydrocohumulone, and tetrahydroadhumulone. In one version of the method, the precipitate is separated from a filtrate, and the precipitate is treated such that the precipitate has an enantiomeric excess of the (+)-tetrahydro-α-acid of greater than 80%, and the filtrate is treated such that a solid recovered from the filtrate has an enantiomeric excess of a (−)-tetrahydro-α-acid of greater than 80%. A reversed solid-liquid process is possible using a different amine.

In another aspect, the invention provides a method for preparing a hop acid. In the method, a racemate of a tetrahydro-α-acid is contacted with an amine to form a precipitate comprising a (+)-tetrahydro-α-acid; and the (+)-tetrahydro-α-acid is isomerized to a hop acid selected from the group consisting of (+)-trans-tetrahydro-iso-α-acids, (−)-cis-tetrahydro-iso-α-acids, and mixtures thereof. The (+)-trans-tetrahydro-iso-α-acid can be selected from (+)-trans-tetrahydro-iso-humulone, (+)-trans-tetrahydro-iso-cohumulone, and (+)-trans-tetrahydro-iso-adhumulone, and the (−)-cis-tetrahydro-iso-α-acid can be selected from (−)-cis-tetrahydro-iso-humulone, (−)-cis-tetrahydro-iso-cohumulone, and (−)-cis-tetrahydro-iso-adhumulone. The amine can be a chiral amine such as (1S,2R)-(−)-cis-1-amino-2-indanol. In one version of the method, the racemate of the tetrahydro-α-acid can be prepared by hydrogenating a β-acid to prepare a desoxy-α-acid, and oxidizing and isomerizing the hydrogenated desoxy-α-acid to prepare the racemate of the tetrahydro-α-acid.

In another aspect, the invention provides a method for preparing group of novel hop acids, (+)-tetrahydro-α-acids isomerized and reduced to a group selected from the group consisting of (+)-hexahydroiso-α-acids, (−)-hexahydroiso-α-acids, and mixtures thereof.

In yet another aspect, the invention provides an additive for flavoring a malt beverage, wherein the additive includes a bittering agent selected from the group consisting of (+)-trans-tetrahydro-iso-α-acids, a (−)-cis-tetrahydro-iso-α-acids, and mixtures thereof. The (+)-trans-tetrahydro-iso-α-acid can be selected from the group consisting of (+)-trans-tetrahydro-iso-humulone, (+)-trans-tetrahydro-iso-cohumulone, and (+)-trans-tetrahydro-iso-adhumulone, and the (−)-cis-tetrahydro-iso-α-acid can be selected from the group consisting of (−)-cis-tetrahydro-iso-humulone, (−)-cis-tetrahydro-iso-cohumulone, and (−)-cis-tetrahydro-iso-adhumulone.

In still another aspect, the invention provides novel ingredients for nutraceutical and functional foods, wherein the active ingredients includes a bittering agent selected from the group consisting of (+)-tetrahydro-α-acids, (+)-trans-tetrahydroiso-α-acids, (−)-cis-tetrahydroiso-α-acids, (+)-trans-hexahydroiso-α-acids, (−)-cis-hexahydroiso-α-acids, and mixtures thereof.

In yet another aspect, the invention provides a method for preparing a hop acid mixture. The method comprises contacting a racemate of tetrahydroiso-α-acids with a chiral amine to form a hop acid complex as a precipitate or in solution such that the hop acid complex has an enantiomeric excess of (+)-tetrahydroiso-α-acids. The enantiomeric excess of the resolved (+)-tetrahydroiso-α-acids can be greater than 50%, preferably greater than 60%, preferably greater than 70%, preferably greater than 80%, and preferably greater than 90%. The resolved tetrahydroiso-α-acids can be enantiomerically pure. The resolved (+)-tetrahydroiso-α-acids can be reduced to a hop acid selected from the group consisting of (+)-trans-hexahydro-iso-α-acids, (−)-cis-hexahydro-iso-α-acids, and mixtures thereof.

In still another aspect, the invention provides a method for preparing a hop acid mixture. The method comprises resolving a racemate of tetrahydroiso-α-acids with a chiral column chromatography to separate an enantiomeric excess of (+)-tetrahydroiso-α-acids. The enantiomeric excess of the resolved (+)-tetrahydroiso-α-acids can be greater than 50%, preferably greater than 60%, preferably greater than 70%, preferably greater than 80%, and preferably greater than 90%. The resolved tetrahydroiso-α-acids can be enantiomerically pure. The resolved (+)-tetrahydroiso-α-acids can be reduced to a hop acid selected from the group consisting of (+)-trans-hexahydro-iso-α-acids, (−)-cis-hexahydro-iso-α-acids, and mixtures thereof.

In yet another aspect, the invention provides an additive for flavoring a malt beverage wherein the additive comprises a bittering agent selected from the group consisting of (+)-trans-tetrahydroiso-α-acids, (−)-cis-tetrahydroiso-α-acids, (+)-trans-hexahydroiso-α-acids, (−)-cis-hexahydroiso-α-acids, and mixtures thereof. In still another aspect, the invention provides a malt beverage including the additive wherein the bittering agent is present in the malt beverage at a level of 1 ppm to 100 ppm.

In still another aspect, the invention provides an active ingredient for a health supplement wherein the ingredient comprises a hop acid selected from the group consisting of (+)-tetrahydro-α-acids, (+)-trans-tetrahydro-iso-α-acids, (−)-cis-tetrahydro-iso-α-acids, (+)-trans-hexahydro-iso-α-acids, (−)-cis-hexahydroiso-α-acids, and mixtures thereof.

These and other features, aspects, and advantages of the present invention will become better understood upon consideration of the following detailed description, drawings and appended claims.

DETAILED DESCRIPTION OF THE INVENTION

Figure 1:
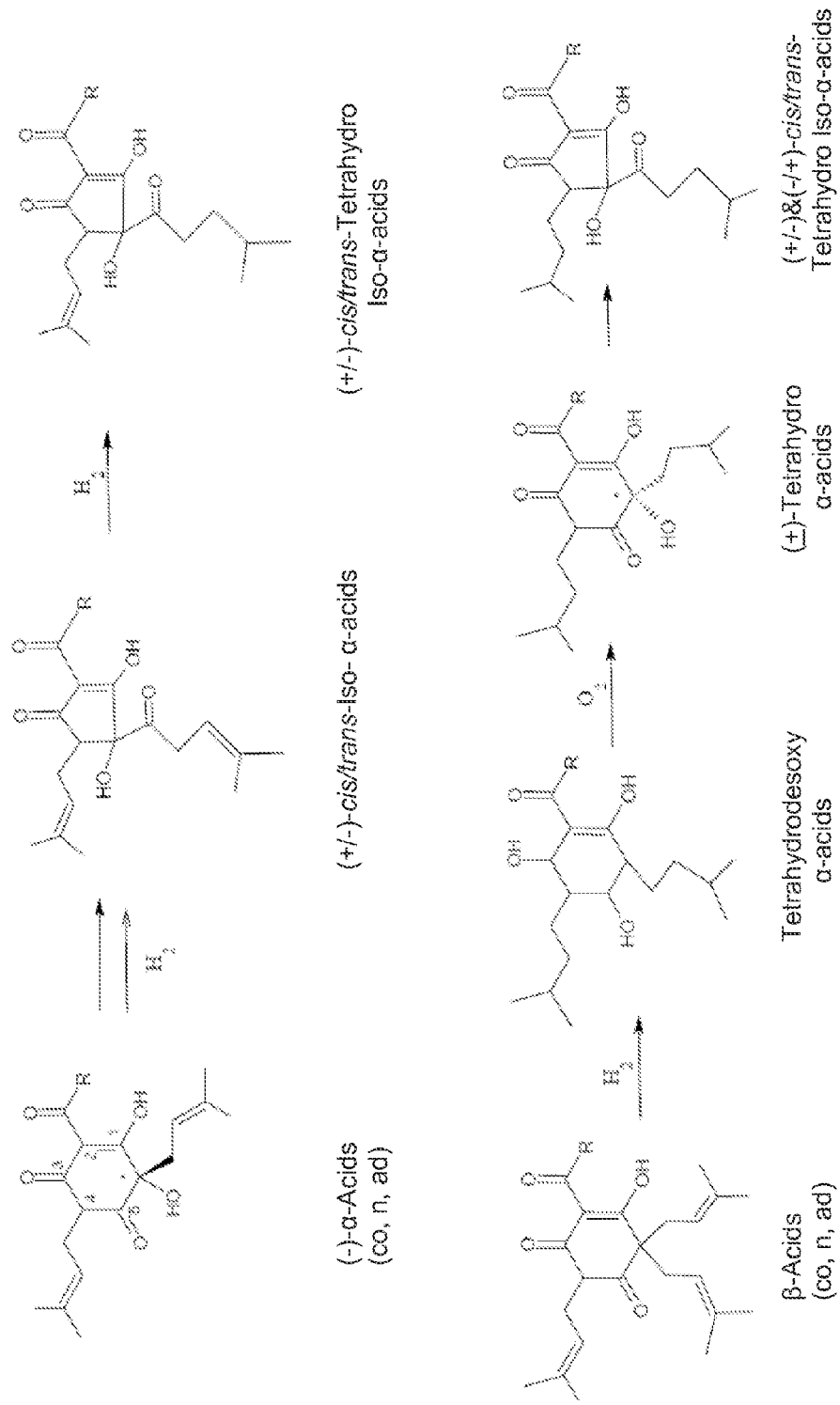
FIG. 1 shows a scheme of tetrahydroiso-α-acids preparation from either α-acids or β-acids.

In one example method of invention, dynamic resolution of a racemic tetrahydro-α-acid mixture has been achieved. Suitable solvents for the resolution can be selected such that at least some of the desired diastereomeric solid precipitates in the solvent and the other member of the pair remains dissolved in the solution. Non-limiting example solvents include substituted or unsubstituted aliphatic or alicyclic hydrocarbons. Some preferred solvents are hexane, cyclohexane and toluene. The solvents and the temperature of the dynamic resolution will vary with the particular hop acid subjected to the resolution.

Precipitation of the desired diastereomeric solid can be achieved with a chiral amine. A preferred amine is one that allows formation of a pair of diastereomeric solids, one member of the pair of diastereomers being at least partially insoluble in the solvent system of the process. A preferred amine is one that allows formation of a pair of diastereomers, one member of the pair being preferentially a precipitate under the reaction conditions. The precipitate can be crystalline or non-crystalline. The chiral amine can be, for example, (1S,2R)-(+)-cis-1-amino-2-indanol. Other chiral amines can be expected to be useful in effecting the resolution of the hop acid.

The less soluble diastereomeric salt from the reaction can be isolated, for example, by filtration, centrifugation, or decantation. For instance, the reaction mixture is cooled to room temperature and the resulting precipitate is recovered by filtration. The filter cake containing the product can be washed with a washing solvent such as an aliphatic hydrocarbon (e.g., hexane). Once isolated, the precipitated diastereomeric salt can be liberated from its complexed chiral amine by reaction with a suitably strong acid. Non-limiting example acids include sulfuric acid, phosphoric acid and hydrochloric acid. The diastereomeric compound that remains in solution in the filtrate can also be isolated with an acid.

Dynamic resolution of the racemate of a tetrahydro-α-acid or racemate of a tetrahydroiso-α-acid in accordance with the invention can produce an enantiomeric excess of the one of the resolved tetrahydro-α-acids or tetrahydroiso-α-acids of greater than 50%, preferably greater than 60%, preferably greater than 70%, preferably greater than 80%, and preferably greater than 90%. The resolved tetrahydro-α-acid or (+)-tetrahydroiso-α-acid can be enantiomerically pure. In one form, the resolved tetrahydro-α-acid is (+)-tetrahydrocohumulone.

The resolved tetrahydro-α-acids can be isomerized to tetrahydro-iso-α-acids by boiling in a suitable solvent such as an ethanol-water mixture, optionally in the presence of a catalyst such as a calcium or magnesium salt. Other isomerization techniques can be used. The tetrahydroiso-α-acid compounds can provide improved flavor, foam, and antimicrobial contributions when added to malt beverages such as beer. In one form, the tetrahydro-iso-α-acid is (+)-trans-tetrahydro-iso-cohumulone or (−)-cis-tetrahydro-iso-cohumulone. The resolved tetrahydro-α-acids can be reduced to (+)-trans-hexahydroiso-α-acids and (−)-cis-hexahydroiso-α-acids.

A variety of optical isomers have been described as having different odor qualities and/or different odor intensities. Such considerations prompted the following experimental study, which aimed to resolve gram quantities of each enantiomer of (±)-tetrahydrocohumulone and to assess their isomerized enantiomers for bitterness, foam quality, and antimicrobial activity. The following Examples are presented for purposes of illustration and not of limitation.

Examples

HPLC of (±)-tetrahydrocohumulone (THCO) and (+/−) and (−/+)-cis/trans-tetrahydroisocohumulones (THICO)

Figure 5:
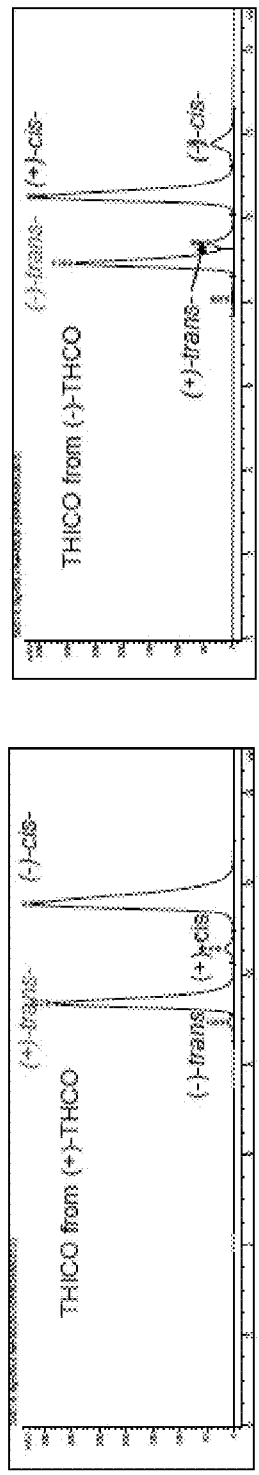
FIG. 5 shows the chiral HPLC separation of isomerized (+) and (−)-THCO (top) and two CD spectra of (+) vs. (−)-trans-THICO (bottom).
Figure 5:
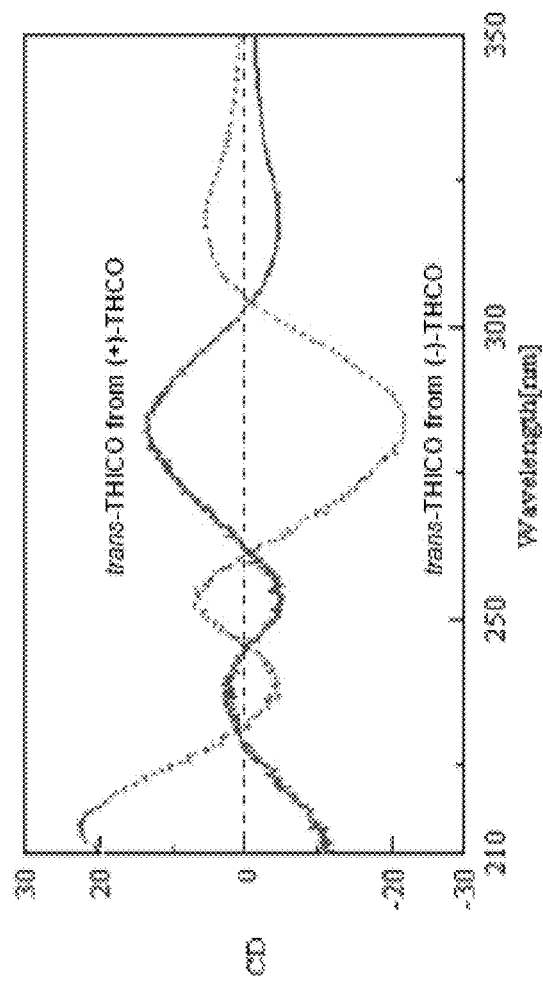

A 5 μm 250×4.6 mm Cyclobond I 2000 column (Advanced Separation Technologies Inc.) was used. To resolve (±)-THCO, an isocratic mixture of 25% A ($CH_3CN$) and 75% B (1% acetic acid+20% methanol/$H_2O$) was used as the mobile phase at a flow rate 1.2 mL/min and detection at 280 nm. Two enantiomers, (−) and (+)-THCO, were eluted, respectively in FIG. 2. (−)-THCO was identified by the hydrogenated α-acids standard. To resolve (±)-cis and (±)-trans-THICO, an isocratic mixture of 35% A ($CH_3CN$) and 65% B (0.01M sodium citrate+20% methanol/$H_2O$) was used as the mobile phase at a flow rate 1.2 mL/min and detection at 254 nm. The elution order was (−)-trans, (+)-trans, (−)-cis, and (+)-cis-THICO identified by the retention times of (+)-cis-THICO and (−)-trans-THICO standards as shown in FIG. 5.

Preparation of Tetrahydrodesoxycohumulone

To a solution of 50 g hexane-crystallized colupulone (0.125 moles) in 250 mL of ethanol was added 10 mL of concentrated sulfuric acid and 5 g of 5% Pd/C catalyst. The mixture was stirred and hydrogenated under 10 psig hydrogen gas in an autoclave. The hydrogenation reaction was completed after 30 min. at 35-50° C. The vessel was purged with nitrogen and the mixture was filtered to give a clear yellow solution of tetrahydrodesoxycohumulone, used directly in the next step.

Oxidation with Peracetic Acid of Tetrahydrodesoxycohumulone to (±)-tetrahydrocohumulone (THCO)

To the above solution was added 23.75 g of 40% peracetic acid (0.125 moles) slowly in a three-neck round bottom flask which was equipped with a thermometer, a condenser, and additional funnel. After addition, the reaction was heated to 50-60° C. for 1 hour and allowed to cool to room temperature. About 100 mL tap water was added and stirred for 1 hour. The ethanol was recovered under vacuum and 200 mL hexane was added to solubilize the THCO in aqueous solution. After a phase separation, the hexane solution was washed with tap water twice to afford 35 g of THCO.

Resolution of (±)-tetrahydrocohumulone (THCO)

To a solution of 11 g of (±)-tetrahydrocohumulone (THCO) (0.031 moles), 20 mL toluene and 300 mL cyclohexane was added 5.5 g of (1S,2R)-(−)-cis-1-amino-2-indanol (AI) (0.037 moles) in 50 mL cyclohexane. The solution was boiled for 15 min. and allowed to cool at room temperature. A yellow solid was crystallized and filtered from the solution. The yellow solid was mixed with 100 mL hexane and 100 mL of 2N HCl. The hexane phase was washed three times with water. After drying with anhydrous magnesium sulfate, the solvent was removed under vacuum to yield 4.65 g of (+)-THCO and confirmed by a chiral HPLC (β-Cyclobond column) with 90% enantiomeric excess (e.e.). The filtrate was acidified with 100 mL of 2N HCl and washed with water three times. After drying with anhydrous magnesium sulfate, the solvent was removed by vacuum to afford 5.3 g of 86% e.e. (−)-THCO and confirmed by β-Cyclobond HPLC.

Isomerization of (+), (−), and (±)-tetrahydrocohumulone (THCO) to cis/trans-tetrahydroisocohumulone To 2.5 g of THCO (7.1 mmoles) and 50 mL ethanol was stirred and heated with 0.3 g NaOH and 43 mg of magnesium sulfate. The isomerization reaction was refluxed for 2 hours and allowed to cool at room temperature. The resulted solution was acidified by 2N HCl and ethanol was recovered by vacuum. The resulted oil was extracted by 50 mL hexane and two phases were separated. The hexane phase was dried by anhydrous magnesium sulfate and the solvent was removed by vacuum to yield enantiomers and a racemate of cis/trans-tetrahydroisocohumulone (THICO).

CONCLUSION (1S,2R)-(−)-cis-1-Amino-2-indano is an unequivocal chiral reagent for resolving racemic hop acids. It reacts with (±)-tetrahydrocohumulones to selectively produce a crystal form of (+)-tetrahydrocohumulone (THCO)/(1S,2R)-(−)-cis-1-amino-2-indano from the solution of (−)-THCO and (1S,2R)-(−)-cis-1-amino-2-indano. It is a dynamic process that can easily process several grams of (±)-tetrahydro-α-acids for any application. The (+)-THCO is a novel bittering precursor as well as its derivatives of (−)-cis/(+)-trans-tetrahydroisocohumulone (THICO). On the other hand, its counterpart, (−)-THCO, is identical to the hydrogenated (−)-cohumulone (a nature α-acid). Three THICO molecules can be enantioselectively distinguished by our receptors, leading to different odor intensities and odor qualities. THICO II from its (+)-THCO have the most bitterness and longest lingering and (±)-THICO III have milder and smooth bitterness than THICO I from (−)-THICO. The foam situation is more complicated by findings of enantioselective effects of each chiral isomer with damaged conformation of LTP (a foam protein) during the kettle boiling. Three THICO I, II, and III molecules demonstrate the same antibacterial effectiveness using the minimum inhibitory concentration (MIC) and the bacterial zone of inhibition (BZI) tests on *Pediococcus damnosus* and *Lactobacillus brevis*. It clearly indicates that the enantioselectively antibacterial interactions between THICO I, II, III and the microbial do not occur.

Results and Discussion

The molecular perception of stereochemistry of tetrahydroiso-α-acids prepared from either α-acids or β-acids is very important because of their potential flavor, foam, antimicrobial contributions in beer. Verzele and De Keukeleire (D. De Keukeleire and M. Verzele, J. Inst. Brewing, 76:265, 1970; "Chemistry and analysis of Hop and Beer Bitter Acids", M. Verzele and D. De Keukeleire, Elsevier, 1991) have established the R-configuration and (−)-optical rotation of α-acids with an asymmetric center at C-6 and also determined the optical properties of their isomerized derivatives denoted as (+)-cis-iso-α-acids and (−)-trans-iso-α-acids. The hydrogenation of either α-acids or isomerized-α-acids retains the chirality, in other words, no optical property is changed. On the other hand, the β-acids prepared tetrahydroiso-α-acids are a racemic mixture consisting of two pairs of (+/−)-cis/trans- and (−/+)-cis/trans-isomers from the isomerization of a racemic mixture of (±)-tetrahydro-α-acids. Because the β-acids are dissymmetric or achiral compounds, the hydrogenolysis/hydrogenation of β-acids produce planar molecules, tetrahydro desoxy-α-acids with a C2 symmetry. At the oxidation step, a chiral center at C-6 is introduced to generate a pair of (±)-tetrahydro-α-acids as shown in FIG. 1.

Resolution by Liquid Chromatography

Ting and Goldstein confirmed the optical rotations of the hydrogenated iso-α-acids as (+)-cis- and (−)-trans-tetrahydroiso-α-acids. (Patrick L. Ting and Henry Goldstein, J. Am. Soc. Brew. Chem. 54(2):103-109, 1996), while a zero value of optical rotations of (±)-cis- and (±)-trans-tetrahydroiso-α-acids is obtained from the β-acids preparation. Ting and Goldstein successfully resolved and assigned (±)-tetrahydro-α-acids using a combination of a semi-preparative C-18 column and an analytical Cyclobond HPLC column (β-Cyclodextrin bonded on 5μ silica gel, a chiral phase column). The column was also used to resolve most of (+) and (−)-enantiomers and diastereomers of total (±)-tetrahydroiso-α-acids.

To evaluate the properties of each enantiomer of tetrahydroiso-α-acids in beer, a gram quantity of substances is needed. Due to the complex compositions of hop bittering compounds (containing at least of 12 compounds with 3 major analogs and 2 diastereoisomers and 2 enantiomers), a strategy of simplifying the resolution process is starting with colupulone, one component of β-acids, to produce (±)-tetrahydrocohumulone. Resolution of (±)-tetrahydrocohumulone (THCO), bittering precursors, should be less complicated than their isomerized (±)-cis- and (±)-trans-tetrahydroisocohumulones (THICO).

Figure 2:
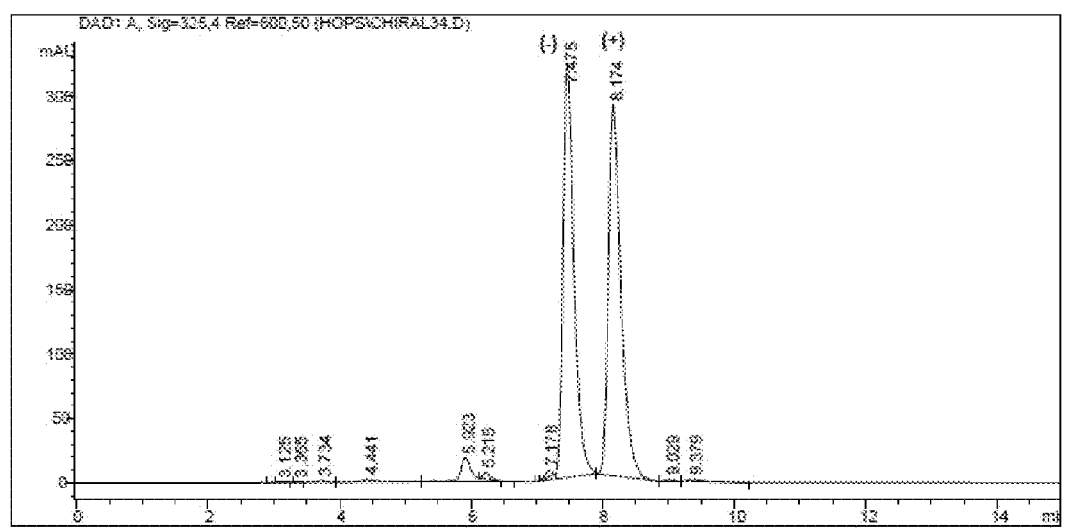
FIG. 2 shows the analytical HPLC resolution of (±)-tetrahydrocohumulone by a 250×4.6 mm β-Cyclobond column with 75% $CH_3CN$+25% of 1% acetic acid in 20% $CH_3OH$/$H_2O$ at 280 nm and 1.2 ml/min.

An analytical chiral HPLC (high pressure liquid chromatography) column (β-Cyclobond) was used to analyze and identify the resolved compounds as shown in FIG. 2. In FIG. 2, (±)-THCO is well-resolved into (−)-THCO identified by authentic (−)-tetrahydro-α-acids and eluted before (+)-THCO. Since a chiral liquid chromatography (LC) was a prevalent technique of resolving enantiomers, two β-Cyclobond 10×2" and 20×2" columns simulated to the analytical conditions were used to separate the racemic mixture of (±)-THCO at milligrams to gram quantities. The resolution of (±)-THCO was poor and ineffective.

Resolution by Dynamic Crystallization

Figure 3:
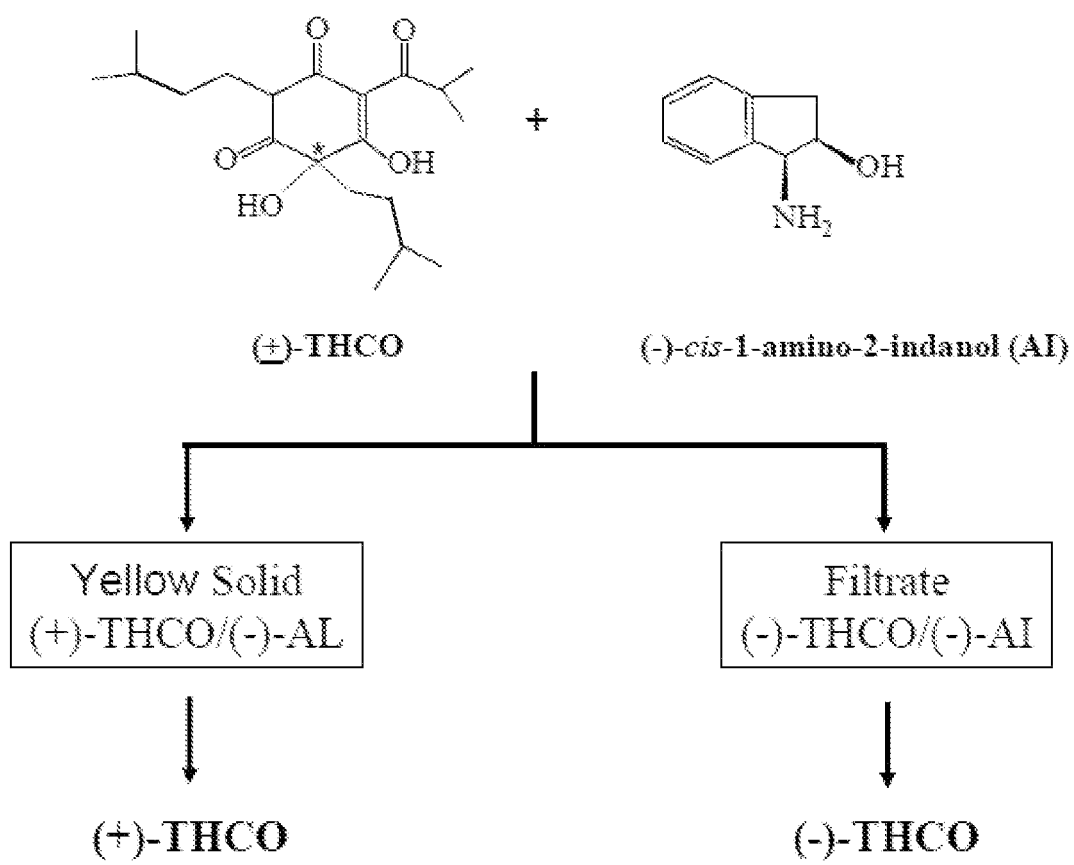
FIG. 3 is a diagram of the dynamic resolution of (±)-THCO.
Figure 4:
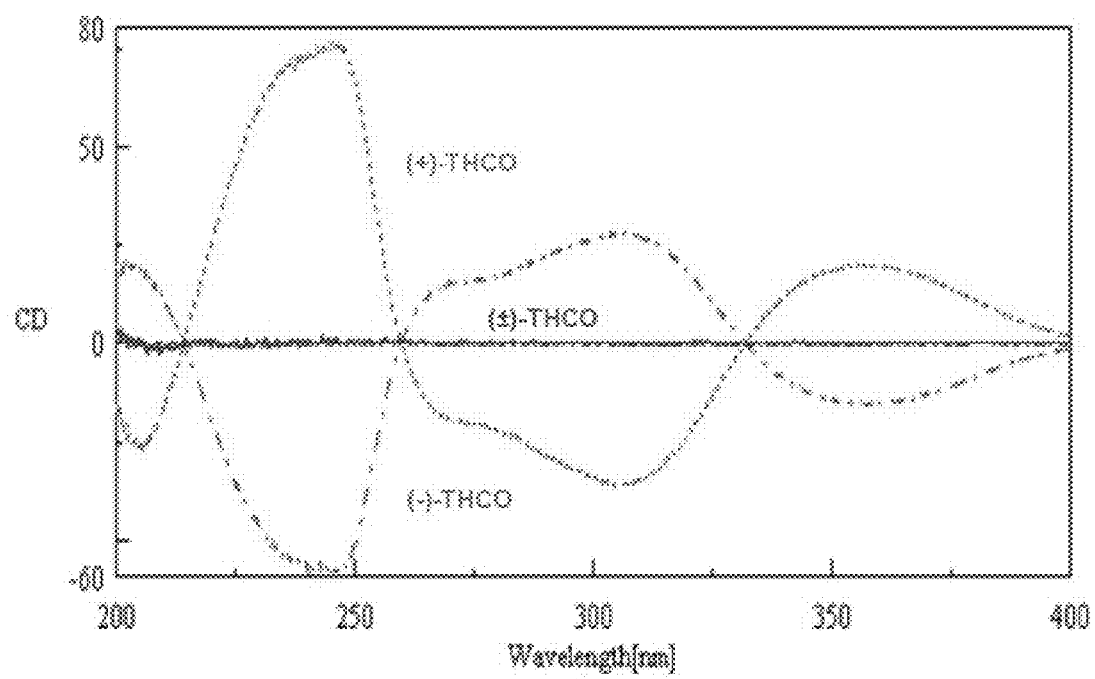
FIG. 4 is a plot of circular dichroism of (±),(+), and (−)-THCO.

Alternatively, using an (−)-alkaloid, (1S,2R)-(−)-cis-1-amino-2-indanol (Al) to react with (±)-THCO becomes a dynamic resolution technique (Chemical & Engineering News, Sep. 9, 2002). Two diastereomeric salts were formed; one, (+)-THCO/(−)-alkaloid, was crystallized out and left one, (−)-THCO/(−)-alkaloid in the solution as shown in FIG. 3. After acidification, it regenerated high optically pure (+) and (−)-THCO, separately, as well as more than gram quantities yield sufficient to perform various tests. A chiral HPLC and CD (Circular Dichroism) confirmed the optical purity and optical spectrum of resolved (+) and (−)-THCO vs. (±)-THCO (FIG. 4). The identity of (−)-THCO were confirmed by comparison of the retention time of chiral HPLC and CD spectrum with the hydrogenated α-acids. The (+)-THCO is a novel bittering precursor having an opposite CD spectrum as (−)-THCO which is a hydrogenated natural α-acid. The isomerization of (+)-THCO produced two novel (−)-cis/(+)-trans-tetrahydroisocohumulone (THICO) in opposite to (−)-THCO produced (+)-cis/(−)-trans-THICO identical to the hydrogenated natural iso-α-acids. FIG. 5 shows a chiral HPLC separation/resolution of (+/−) and (−/+)-cis- and trans-THICO and two CD spectra of (+)- and (−)-trans-THICO. The bitter perception, foam quality, and antimicrobial activity of three molecules and their derivatives of (+/−)-cis/trans-THICO (THICO I), (−/+)-cis/trans-THICO (THICO II), and (±)-cis/trans-THICO (THICO III) were investigated, respectively.

Bitterness Perception

An aqueous 5% v/v ethanol/$H_2O$ solution was spiked with 6 ppm of THICO I, II, and III. The bitterness of three molecular perceptions is summarized in Table 1. It indicates that the bitterness intensity is II>III>I and the bitter perception of III is smooth and milder than the others.

TABLE 1

| Bitterness of three THICO I, II, and III in 5% ethanol/$H_2O$ | | |
|---|---|---|
| THICO I (natural) | THICO II (novel) | THICO III (racemic) |
| Less bitter at back of tongue, harsh, slight lingering | Most bitter and lingering, astringent, bitter in whole mouth | Stronger than I, but similar, smooth, milder, clean bitterness |

Two sets of unhopped lagers (A and B) were spiked with 6 ppm and 13 ppm of THICO I, II, and III, respectively. A C-18 reversed phase HPLC analysis of cis/trans-THICO present in each beer is shown in Table 2.

TABLE 2

| HPLC analysis of cis/trans-tetrahydroisocohumulones (THICO) in Beer | | | |
|---|---|---|---|
| | THICO I (ppm) | THICO II (ppm) | THICO III (ppm) |
| A | 5.6 | 6.0 | 6.0 |
| B | 13.7 | 12.2 | 13.8 |

Sensory evaluation indicated that beer with THCO II was noted as having the strongest initial bitterness and lingered the longest. The other two beers were noted as being similar with the THICO I having a little more initial bitterness and the bitterness in the THICO III beer diminished quickly. In set B, THICO II beer had a strong initial bitterness that increased (described as late bitterness) and also lingered. The other two beers were noted as being similar with initial intense bitterness that diminished slowly with slight lingering bitterness. It indicates that our odor receptors can differentiate two enantiomeric THICO I and II, leading to differences in bitter strength and quality.

Foam

One major factor of beer foam is an interaction of a lipid transfer protein (LTP) from barley with the hop bittering compounds. (see, L. Lusk, H. Goldstein, D. Ryder, J. Amer. Soc. Brew. Chem. 53(3):93-103, 1995). Tetrahydroiso-α-acids interact preferentially with LTP due to their greater hydrophobicity. (see, K. Takeshi and T. Shellhammer, *J. Agric. Food Chem.*, 2008, 56 (18), pp 8629-8634). The Nibem and half-life foam test of three bittering molecules in beers in set A do not show any significant differences (see Table 3). Discrepancy of the enantioselective effects between enantiomers of THICO and LPT is not clear in the beer foam formation. It might be due to disruption of the conformation of LPT which has been known to be damaged after long kettle boiling (Sandra N. E. Van Nierop, David E. Evans, Barry C. Axcell, Ian C. Cantrell, and Marina Rautenbach, J. Agric. Food Chem., 2004, 52 (10), pp 3120-3129; E. N. Clare Mill, Chunli Gao, Peter J. Wilde, Neil M. Rigby, Ramani Wijesinha-Bettonis, Victoria E. Johnson, Lorna J. Smith and Alan R. Mackie, Biochemistry, 2009, 48 (51), pp 1208-12088).

TABLE 3

Results of beer foam and bittering molecules

|  | Nibem 30 sec. | Half-Life |
|---|---|---|
| THICO I | 255 | 4.7 |
| THICO II | 259 | 5.0 |
| THICO III | 246 | 5.3 |

Antimicrobial Activity of THICO I, II, III and Minimum Inhibitory Concentration (MIC) and Bacterial Zone of Inhibition (BZI)

The antimicrobial effect of three molecules was tested on *Pediococcus damnosus* and *Lactobacillus brevis* with two methods (MIC and BZI). MIC was determined based on the concentration at which no bacteria were detected in the modified BMB without Tween 80 culture medium. The result is summarized in Table 4 and the MIC is 16 ppm for both THICO I and II. The average diameters of the zones of bacterial inhibition in Universal Beer Agar (UBA) produced by the filter paper disks immersed in 4000 ppm of THICO I, II, and III in 70% ethanol/water are shown in Table 5. Zone diameters increased with the same rates for three molecules on two different organisms (*Pediococcus damnosus* and *Lactobacillus brevis*) indicate that all molecules have the same antibacterial effectiveness. No enantioselective antibacterial interactions between THICO I, II, III and the microbial occur.

TABLE 4

Minimum inhibitory concentration of THICO I and II
*Pediococcus damnosus*
Minimum Inhibitory Concentration of Hop Acids in 70% Ethanol

| | ppm | | | | | | | | |
|---|---|---|---|---|---|---|---|---|---|
| | 128 | 64 | 32 | 16 | 8 | 4 | 2 | 1 | 0.5 | 0 |
| THICO I | − | − | − | +/− | + | + | + | + | + | + |
| THICO II | − | − | − | +/− | + | + | + | + | + | + |

+ = Growth of beer spoilage bacteria
− = No growth of beer spoilage bacteria
+/− = Partial inhibition of bacterial growth

TABLE 5

Antimicrobial effect of THICO I, II, and III on bacterial
Diameter of Bacterial Zone of Inhibition (mm)

| | *Pediococcus damnosus* | *Lactobacillus brevis* |
|---|---|---|
| Control | 0 | 0 |
| THICO I | 11.5 | 26 |
| THICO II | 12 | 26.5 |
| THICO III | 12 | 22.5 |

Thus, in the present invention, resolution of a racemic (±)-tetrahydrocohumulone (or tetrahydro-α-acid) and their isomerized tetrahydroisocohumulones (or tetrahydroiso-α-acid) has been achieved in gram quantity by a dynamic crystallization with (1S,2R)-(−)-1-amino-2-indanol. The resolved (+)-tetrahydrocohumulone (THCO) is a novel bittering precursor while the (−)-THCO is identical to the hydrogenated (−)-cohumulone (a natural α-acid). Both enantiomers are isomerized to the same molecular structures, but with opposite optical rotations. The (+)-THCO is converted into two novel bittering diastereomers, (−)-cis- and (+)-trans-tetrahydro isocohumulone (THICO II) while (−)-THCO is converted into (+)-cis- and (−)-trans-THICO (THICO I) identical to the hydrogenated cis and trans-isocohumulone (a natural iso-α-acid).

Sensory indicates that the bitter intensity of three molecules is THICO II>(±)-THICO III>THICO I. The perception of (±)-THICO III is smooth, clean and milder than I and II. In the foam situation, it seems no apparent foam quality differences among three molecular beers. In other words, no clear discrepancy of enantioselective effects among three molecules and lipid transfer protein (LTP) is found. It may be due to destruction of LTP conformation during long kettle boiling.

The minimum inhibitory concentration (MIC) of THICO I and II is similar at 16 ppm against *Pediococcus damnosus*. Zone diameters increased with the same rates for three THICO I, II, and III molecules on two different organisms (*Pediococcus damnosus* and *Lactobacillus brevis*) indicate that all exhibit the same antibacterial effectiveness or no enantioselective antibacterial effect among THICO I, II, III and the microbial.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for preparing a hop acid mixture, the method comprising:
   contacting a racemate of tetrahydro-α-acids with a chiral amine to form a hop acid complex as a precipitate or in solution, the hop acid complex having an enantiomeric excess of (+)-tetrahydro-α-acids,
   wherein the amine is (1S,2R)-(−)-cis-1-amino-2-indanol.

2. The method of claim 1 further comprising:
   isomerizing the (+)-tetrahydro-α-acids to hop acids selected from the group consisting of (+)-trans-tetrahydro-iso-α-acids, (−)-cis-tetrahydro-iso-α-acids, and mixtures thereof.

3. The method of claim 1 further comprising:
   isomerizing and reducing the (+)-tetrahydro-α-acids to hop acids selected from the group consisting of (+)-trans-hexahydro-iso-α-acids, (−)-cis-hexahydro-iso-α-acids, and mixtures thereof.

4. The method of claim 2 further comprising:
   reducing the (+)-tetrahydroiso-α-acids to hop acids selected from the group consisting of (+)-trans-hexahydro-iso-α-acids, (−)-cis-hexahydro-iso-α-acids, and mixtures thereof.

5. The method of claim 1 further comprising:
   treating the hop acid complex to prepare a solid having an enantiomeric excess of the (+)-tetrahydro-α-acids of greater than 50%.

6. The method of claim 1 further comprising:
   treating the hop acid complex to prepare a solid having an enantiomeric excess of the (+)-tetrahydro-α-acids of greater than 80%.

7. The method of claim 1 wherein:
   the racemate of the tetrahydro-α-acid is prepared by hydrogenating a β-acid to prepare a desoxy-α-acid, and oxidizing and isomerizing the hydrogenated desoxy-α-acid to prepare the racemate of the tetrahydro-α-acid.

8. The method of claim 7 wherein:
   the β-acid is colupulone, and
   the desoxy-α-acid is tetrahydrodesoxycohumulone.

9. The method of claim 1 wherein:
   the tetrahydro-α-acid is selected from tetrahydrohumulone, tetrahydrocohumulone, and tetrahydroadhumulone.

10. A method for preparing a hop acid mixture, the method comprising:
    contacting a racemate of tetrahydroiso-α-acids with a chiral amine to form a hop acid complex as a precipitate or in solution, the hop acid complex having an enantiomeric excess of (+)-tetrahydroiso-α-acids,
    wherein the amine is (1S,2R)-(−)-cis-1-amino-2-indanol.

11. The method of claim 10 further comprising:
    reducing the (+)-tetrahydroiso-α-acids to hop acids selected from the group consisting of (+)-trans-hexahydro-iso-α-acids, (−)-cis-hexahydro-iso-α-acids, and mixtures thereof.

12. The method of claim 10 further comprising:
    treating the hop acid complex to prepare a solid having an enantiomeric excess of the (+)-tetrahydroiso-α-acids of greater than 80%.

* * * * *